United States Patent [19]

Bohl

[11] 4,441,356
[45] Apr. 10, 1984

[54] TEMPERATURE ACTUATED AIR FLOW CONTROL AND GAS SAMPLER

[75] Inventor: Thomas L. Bohl, Madison, Ohio

[73] Assignee: The Babcock & Wilcox Company, New Orleans, La.

[21] Appl. No.: 362,926

[22] Filed: Mar. 29, 1982

[51] Int. Cl.$^3$ .................. G01N 1/24; G01N 27/14
[52] U.S. Cl. .................................. 73/23; 73/27 R; 73/864.34; 137/468; 236/93 R
[58] Field of Search .............. 73/27 R, 23, 864.34; 137/468; 236/93 R, 101 E

[56] References Cited

U.S. PATENT DOCUMENTS

| | | | |
|---|---|---|---|
| 2,720,108 | 10/1955 | Johnson | 73/27 R |
| 4,038,034 | 7/1977 | Nakajima et al. | 137/468 |
| 4,134,289 | 1/1979 | Bohl et al. | 73/864.34 |
| 4,140,275 | 2/1979 | Inada | 236/101 E |

Primary Examiner—Stephen A. Kreitman
Attorney, Agent, or Firm—Vytas R. Matas; Robert J. Edwards

[57] ABSTRACT

A temperature actuated air flow control comprises a fluid inlet for the gas sample which is connected to an exhaust line through an intermediate venturi chamber into which a gas such as air is vented in order to aspirate the flow of the gas through the inlet to the exhaust. The amount of flow of the aspirating gas controls the quantity of flow of the sample gas through the inlet to the exhaust. A valve chamber in the aspirating gas passage comprises a bimetallic plate which is flexed between a position in which it closes a flow passage for the aspirating gas to one in which it opens the passage. The bimetallic plate is flexed by temperature change. The device advantageously functions to provide for the inflow of a sample or test quantity of a gas and flows through a chamber having a gas sensor to determine the characteristics of the gas and is directed through a venturi section and out through an exhaust. An aspirating gas such as air is directed into the venturi section and its quantity is controlled by the bimetallic element. In a correct operating temperature the bimetallic element will be flexed to open the passage and permit the continuous sampling of the gas but if the temperature falls for example to a temperature which is below the dew point of the sample gas the bimetallic element may be chosen so as to close off the aspirating air and stop the testing at that time.

6 Claims, 3 Drawing Figures

TEMPERATURE ACTUATED AIR FLOW CONTROL AND GAS SAMPLER

FIELD AND BACKGROUND OF THE INVENTION

This invention relates in general to flow control devices and in particular to a new and useful gas flow control device for a gas sampler apparatus.

The present invention has application to the control of all fluids which require a reduction of flow or a turn-off of the flow due to certain temperature changes. The invention has particular application in the construction of a gas analyzer which uses heated sampling systems to prevent liquid condensation in the system and that draw a gas through the system by using an aspirating gas such as air to effect the flow. It is desirable with such devices to interrupt the aspirator gas flow when the sampling components temperatures fall below the dew point of the sample gas. Conventional means use a temperature sensor and a control with a gas solenoid valve which controls the aspirating air stream. Such an arrangement involves expensive electrical circuitry and connections and piping and frequently limits its applicability due to the ambient condition effects on the valve and electrical components.

SUMMARY OF THE INVENTION

In accordance with the present invention the flow of an aspirating gas and hence the flow of a control gas is regulated by use of a snap action bimetallic part and is arranged in a chamber of the apsirator inlet passage and regulates the flow of the aspirated gas easily and automatically. The bimetallic part is advantageously a disc or similar element which has an area which overlies and closes the aspirator air passage whenever the temperature of operation is not in a satisfactory range. The bimetallic elements are chosen to achieve the desired temperature range and if the bimetallic element is located in an aspirated chamber where it is not appreciably cooled by the temperature of the aspirating air will provide a representative sensing of the temperature of the critical sampling compounds. A simple bimetallic device will accomplish the same function as an electrical control valve but will be much less expensive and much easier to install and operate.

Accordingly it is an object of the invention to provide an improved temperature actuator fluid control in which a sample gas flow is regulated by the flow of an aspirating gas and this aspirating gas flow is controlled by a bimetallic element which will close off the flow when the desired temperature is not achieved.

A further object of the invention is to provide a gas sampler device which includes a connecting passage between an inlet for the sample gas to an outlet for the gas which has a venturi or reduced area section through which an aspirating gas is directed through a chamber for the gas which has a bimetallic element therein which permits flow of the aspirating gas only in a desired temperature range.

A further object of the invention is to provide a temperature actuated fluid flow control and a gas sampler which are simple in design, rugged in construction and economical to manufacture.

The various features of novelty which characterize the invention are pointed out with particularity in the claims annexed to and forming a part of this disclosure. For a better understanding of the invention, its operating advantages and specified objects attained by its uses, reference is made to the accompanying drawings and descriptive matter in which preferred embodiments of the invention are illustrated.

DETAILED DESCRIPTION OF PREFERRED EMBODIMENTS

Figure 1:
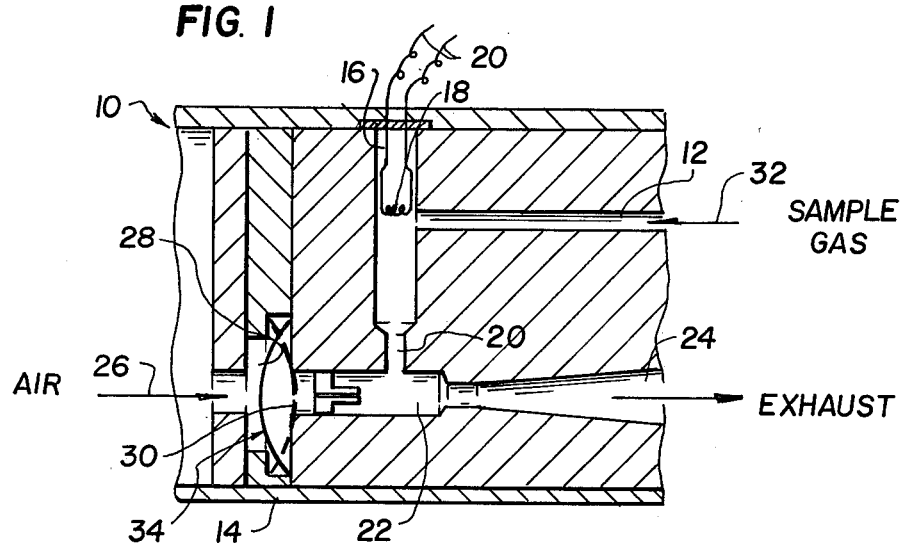
FIG. 1 is a partial sectional view of a gas sampling device constructed in accordance with the invention.
Figure 2:
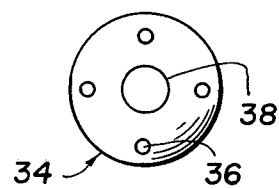
FIG. 2 is an elevational view of a bimetallic element for the control of the aspiration gas in the device shown in FIG. 1.

Referring to the drawings in particular, the invention embodied therein in FIGS. 1 and 2 comprises temperature actuated fluid flow control device generally designated 10 which in the embodiment illustrated comprises a device for sampling a gas and which includes an inlet passage 12 for the inflow of a gas sample into a heated block or housing 14 which contains a separate sampling chamber 16 having a gas sensing device 18 which may for example include means for determining the type of gas and possibly also the quantity of such gas in a particular flow situation. As shown the gas sensor 18 is connected through electrical lines 20 to suitable instruments for determining the desired gas characteristics. The sample gas then flows through a reduced flow area section 20 followed by an aspirating chamber 22 and then out through an exhaust or discharge 24. The flow of the sample gas through the inlet 12 is controlled by the flow of an aspirating gas which is admitted in the direction of an arrow 26 into an aspirating gas flow control chamber 28 through an opening 30 into the chamber 22 and then out the exhaust 24 and its flow induces the flow of the sample gas through the inlet 12.

The flow of the sample gas in the direction of arrow 32 is controlled by the flow of the aspirated gas in the direction of the arrow 26 through the opening 30. For this purpose a bimetallic element 34 is disposed in the aspirating chamber 28 and it may be flexed from the solid line position indicated to the dotted line position in accordance with temperature changes. The bimetallic element is made up of metals having characteristics which will permit it to operate in the desired temperature range and it is advantageously in the form of a disc as indicated in FIG. 2 or as a disc having flaps as indicated at 34' in FIG. 3. The construction may be of any shape such that it will close the opening 30 when the temperature is other than a correct operating temperature. The element is located in the chamber 28 where it is not appreciably cooled by the temperature of the aspirating air and will sense the temperature of the critical sampling gas entering in the direction of the arrow 32. In the embodiment of FIGS. 1 and 2 bimetallic element 34 includes a plurality of openings 36 defined in a marginal area adjacent its periphery or outwardly of an area 38 of the bimetallic element which may be positioned so that it will completely close the opening 30 when it is flexed to a dotted line position as shown in FIG. 1. In the solid line position as shown in FIG. 1 the openings 36 will permit the flow of the aspirating gas therethrough and into the opening 30 for flow through the chamber 22 to the exhaust 24.

In the embodiment of the invention shown as a gas analyzer when the block 14 is at proper operating temperature the element will remain in the solid line position and permit flow of aspirating gas and inflow of the sample gas in the direction of the arrow 32. If the block temperature cools below the desired temperature the bimetallic element abruptly changes to the dotted line position thereby blocking air flow to the aspirator and shutting off the sampling process. In so doing it eliminates the possibility of condensate forming in the gas passageway.

The bimetallic elements 34 are well known elements and are fabricated by bonding two metals together which have different thermal coefficients of expansion. By proper selection of metals and diameters and sizes, etc. the element can be made to deflect abruptly in order to rapidly cause displacement or exert forces.

Figure 3:
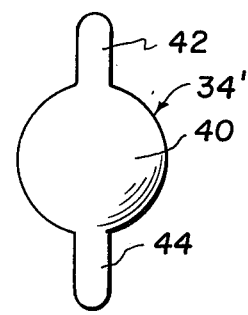
FIG. 3 is a view similar to FIG. 2 of another embodiment of the invention.

In the embodiment of FIG. 3 a solid central area 40 of the bimetallic element 34' is of a size in which it will close off the opening 30 in the dotted line position. When it is flexed outwardly to the solid line position the flaps 42 and 44 provide a free flow area therebetween around the solid part 40 in the operating position of the gas sampler.

While specific embodiments of the invention have been shown and described in detail to illustrate the application of the principles of the invention, it will be understood that the invention may be embodied otherwise without departing from such principles.

What is claimed is:

1. A temperature actuated fluid flow control, comprising a fluid inlet, an exhaust line for the fluid connected to said fluid inlet, a reduced flow area section in the connection of said exhaust line to said fluid inlet, an aspirating fluid connection line extending into the connection adjacent said reduced area for supplying aspirating fluid to induce flow of fluid into said inlet and out said exhaust line, said aspirator fluid connecting line having a throughflow chamber with an opening for the passage of the aspirating gas, a bimetallic valve plate disposed in said chamber and overlying the opening and being flexible and responsive to temperature change so that in a first flexed position it closes the opening to stop the flow of aspirating gas whenever the dewpoint temperature of the fluid is reached and movable to another flexed position by temperature change to open the opening whenever the fluid temperature is above the dewpoint of the fluid.

2. A temperature actuated fluid flow control according to claim 1, wherein said bimetallic valve plate includes a central solid area which in one flexed position is large enough to cover the opening and a marginal area having openings therein for the flow of the aspirating gas therethrough.

3. A temperature actuated fluid flow control according to claim 1, wherein said bimetallic element comprises a plate having diametrically opposite flaps and a central solid area of a size sufficient to close the opening.

4. A temperature actuated fluid flow control comprising a housing defining a heated block, a gas sensor disposed in said housing, a fluid inlet, an exhaust line for fluid connected to said fluid inlet with said gas sensor being connected to both said fluid inlet and said fluid outlet, a reduced flow area section in the connection of said exhaust line to said fluid inlet, an aspirating fluid connection line extending into the connection adjacent said reduced area for supplying aspirating fluid to induce flow of fluid into said inlet and out said exhaust line, said aspirator fluid connecting line having a throughflow chamber with an opening for the passage of the aspirating gas, a bimetallic valve plate disposed in said chamber and overlying the opening and being flexible and responsive to temperature change so that in a first flexed position it closes the opening to stop the flow of aspirating gas and movable to another flexed position by temperature change to open the opening, and said aspirating gas comprising air.

5. A temperature actuated fluid flow control according to claim 4, wherein said gas sensor includes a chamber disposed in said heated block housing connected to said fluid inlet and having a separate connection to said exhaust line, means in said sensing chamber for sensing a characteristic of said gas.

6. A gas sampling device comprising means defining a gas sampling chamber, a gas sensor in said chamber, a sample gas inlet connected into said chamber, an aspirating gas line connected between said chamber and said exhaust line, said aspirating gas line including an aspirating gas chamber having an aspirating gas inlet and an aspirating gas discharge leading to said aspirating gas connection, a bimetallic valve element disposed in said aspirating gas chamber and overlying the opening and being flexible and responsive to temperature change so that in a first flexed position it closes the opening to stop the flow of aspirating gas and is movable to another flexed position by temperature change to open the opening.

* * * * *